United States Patent [19]

Duffy

[11] Patent Number: 5,306,811
[45] Date of Patent: Apr. 26, 1994

[54] SQUAMOUS CELL CARCINOMA-LIKE IMMUNOREACTIVE ANTIGEN FROM HUMAN FEMALE URINE

[75] Inventor: Thomas H. Duffy, Santa Ana, Calif.

[73] Assignee: Ciba Corning Diagnostics Corp., Medfield, Mass.

[21] Appl. No.: 994,399

[22] Filed: Dec. 21, 1992

Related U.S. Application Data

[62] Division of Ser. No. 618,774, Nov. 27, 1990, abandoned.

[51] Int. Cl.$^5$ .......................... C07K 3/02; C07K 3/20; C07K 15/14
[52] U.S. Cl. .................................... 530/412; 530/350; 530/395; 530/413; 435/7.23
[58] Field of Search ................. 436/543; 435/7.1, 7.23; 530/395, 412, 413, 350

[56] References Cited

FOREIGN PATENT DOCUMENTS 0338846 of 0000 European Pat. Off. .
0363703 of 0000 European Pat. Off. .
62-084100 4/1987 Japan .......................... A61K 39/00
9106866 of 0000 World Int. Prop. O. .

OTHER PUBLICATIONS

Kato, H. et al. (77) Cancer 40:1621–1628.
Cancerlit, Abstract 90058421, Zhau, H. E. et al.: "A 180-KD Protein Marker for Human Bladder Cancer", & J. Urol., 141 (4, Part 2) 318A 1989.
Duffy, T. H. and Bales, R. M., Tumor Markers in Seminal Plasma and Amniotic Fluid, 35 Clin. Chem. (1989) 1079.
Kato, H.; Morioka, H.; Aramaki, S. and Torigoe, T., Radioimmunoassay for Tumor-Antigen of Human Cervical Squamous Cell Carcinoma, 25 Cellular and Molecular Biology (1979) 51–56.
Kato, H.; Morioka, H.; Tsutsui, H.; Aramaki, S. and Torigoe, T., Value of Tumor-Antigen (TA-4) of Squamous Cell Carcinoma in Predicting the Extent of Cervical Cancer, 50 Cancer (1982) 1294.
Kato, H.; Morioka, H.; Aramaki, S.; Tamai, Kind Torigoe, T. Prognostic significance of the tumor antigen TA-4 in squamous cell carcinoma of the uterine cervix, 145 Am. J. Obstet. Gynecol. (1983) 350.
Kato, H.; Tami, K.; Morioka, H.; Nagai, M.; Nagaya, T. and Torigoe, T. Tumor-Antigen (TA-4) in the Detection of Recurrence in Cervical Squamous Cell Carinoma, 54 Cancer (1984) 1544.
Maruo, T.; Shibata, K.; Kimura, A.; Hoshina, M. and Mochizuki, M. Tumor-associated antigen, TA-4, in the monitoring of the effects of therapy for squamous cell carcinoma of the uterine cervix, 56 Cancer (1985) 302.
Morioka, H.; Tumor Antigen (TA-4) of Squamous Cell Carcinoma-Its Tissue Distribution and Its Relationship to Serum TA-4 Concentrations, 6 Asia-Oceania Journal of Obstetrics and Gynecology (1980) 91.

Primary Examiner—Kay K. Kim
Attorney, Agent, or Firm—Arthur S. Morgenstern; Nicholas I. Slepchuk, Jr.

[57] ABSTRACT

A squamous cell carcinoma-like (SCC-like) immunoreactive antigen has been identified in human female urine. This material appears to perform the same as and quite likely have the same composition as squamous cell carcinoma associated antigen (SCC) which is a subfraction of tumor antigen 4 (TA-4). This patent also relates to the isolation, and use, of the SCC-like material.

5 Claims, No Drawings

SQUAMOUS CELL CARCINOMA-LIKE IMMUNOREACTIVE ANTIGEN FROM HUMAN FEMALE URINE

This is a divisional of copending U.S. patent application Ser. No. 07/618,774 filed on Nov. 27, 1990 now abandoned.

SUMMARY OF THE INVENTION

A squamous cell carcinoma-like (SCC-like) immunoreactive antigen has been identified in human female urine. This material appears to perform the same and quite likely to have the same composition as squamous cell carcinoma associated antigen (SCC) which is a subfraction of tumor antigen 4 (TA-4). This invention also relates to the isolation, and use, of the SCC-like material.

BACKGROUND OF THE INVENTION

There is considerable literature on the existence of squamous cell carcinoma and the diagnostic value of a tumor antigen of the squamous cell carcinoma (often referred to as TA-4 or its subfraction SCC).

The SCC antigen and TA-4 which have been referred to in the literature have been extracted from either the actual squamous cell carcinoma itself, a carcinoma cell line derived therefrom or from serum which is found in patients who have squamous cell carcinoma. There are inherent difficulties in using these materials, namely the difficulty and hazard of handling the actual carcinoma tissue and the low concentration of TA-4 which appears in serum or cell lines. Thus the difficulty in handling the current sources of these antigens makes the production of these materials and of products utilizing the SCC antigen and TA-4 (e.g., reference materials) very difficult and expensive.

Previous work by the current inventor (35 Clin. Chem. (1989) 1079) also identified SCC-like material in seminal plasma and amniotic fluid. Although present in concentrations above that found in serum, the difficulty of obtaining these fluids make them impractical as commercial sources.

This invention relates to the identification of an SCC-like material in human female urine. This material is present in urine in a much higher level than that in normal human serum and can be isolated without encountering the difficulties of handling the other human materials. The identification of the SCC-like material in urine has led to the ability to isolate a material which is much less expensive to produce than the previous materials and methods and which has been found to be as useful as the previous materials.

The invention covers not only the identification of the material but also techniques for isolation and use of the SCC-like material.

DETAILED DESCRIPTION OF THE INVENTION

This invention covers the identification of a novel source for squamous cell carcinoma-like (SCC-like) immunoreactive antigen, a material which has been found to perform the same and, so far as can be ascertained by the determination of molecular weight and isoelectric point, to be the same composition-wise as squamous cell carcinoma associated antigen (SCC). This invention also relates to the isolation of, and use of, the SCC type material.

Urine was collected from human subjects and analyzed to determine the presence of the SCC material. (See examples hereafter.) To analyze the urine a commercially available radioimmunoassay technique was used (Product SCC-RIA, Catalog #1376-22, purchased from Abbott Laboratories, Diagnostics Div., North Chicago, IL), wherein a competitive immunoassay was used. In the assay, radiolabelled SCC and the urine sample competed with an antibody provided by the commercial kit. It was found that the SCC-like material is present in human female urine at a level much higher than that found in human serum and in human male urine. Levels in female human urine were found to range from approximately 40 ng/ml up to nearly 500 ng/ml, while that found in normal human serum is less than 2.5 ng/ml. In human serum a concentration of above 2.5 ng/ml has been associated with a cancerous state. (Kato et al, 50 Cancer (1982) 1294) Levels of SCC-like material in the male urine were found to be low (i.e., approximately 3 ng/ml or less). The fact that the competitive immunoassay detected the substance in the urine indicated that the material is similar if not identical in immunologic properties to the authentic SCC antigen.

To determine the composition of the SCC-like material, it was compared to the reference material provided in the Abbott immunoassay kit via the use of several common techniques, namely gel filtration and ion exchange techniques (See Examples 4 and 5). The results of these tests showed that the SCC-like material from human female urine was the same as authentic SCC material extracted from carcinoma tissue. Thus utilizing the techniques described above, the SCC material from human female urine was found to be the same physically and to perform the same in immunoassay techniques as the authentic SCC material.

In addition, further work was done to isolate the material from human female urine. Once the samples containing high levels of SCC-like material were identified, samples were concentrated (See Examples 6 and 7) and lyophilized.

Once the SCC-like material was isolated it was then utilized in a number of applications where SCC from malignant tissue had been used by other laboratories, namely to develop materials which could be used as controls for clinical assays for the quantitative and qualitative measurement of SCC antigen in human serum.

The above describes the best mode contemplated by the inventor for the isolation of and use of the SCC-like material. However, it is contemplated that SCC-like materials could be substituted for authentic SCC in all analytical procedures including, without limitation, radioimmunoassay, ELISA, and other analytical techniques. For example, most immunoassays, for the identification of an antigen, utilize either a labelled antigen or a labelled antibody. SCC-like antigen or antibody could be labelled using various established techniques, for example, the addition of a radioactive label, an enzymatic label, a fluorescent label, a chemiluminescent label or other labels which would make the material useful in an immunochemical analytical technique. These would serve as the reporting groups in the immunoassays. Standards or calibrators are also usually needed which contain known concentrations of the desired antigen. SCC-like material from human female urine, or antibodies produced therefrom could provide an inexpensive source for these constituents. It is also contemplated that human female urine might be concentrated and utilized, or perhaps even utilized without concentration, in other analytical techniques where authentic SCC itself might currently be used.

It is further contemplated that the SCC-like material could be used as an immunogen to develop an antibody. Polyclonal, monoclonal or other antibodies could be raised against the SCC-like material. The technology for production of antibodies (polyclonal or monoclonal) has been well established. For production of polyclonal antibodies, the human SCC-like material could be injected into the desired animal (usually rabbit) to produce an immunogenic response. The animal's serum would then be used as a source of antibody to SCC. It would be especially useful to have large quantities of purified SCC, to use as the immunogen, in order that the animals would produce only antibodies specific for SCC and not for extraneous proteins. For production of monoclonal antibodies, the human SCC-like material could be injected into the desired strain of mouse (or other animal when the technology becomes established), immortal antibody secreting cell lines produced, and these cell lines screened for SCC recognition. Once again large quantities of purified SCC would cut the screening time as well as greatly increase the chances of obtaining a cell line secreting antibody specific for SCC.

Techniques are well known by those expert in the field for producing antibodies (monoclonal, polyclonal, etc.). See, for example, Koehler, G. and C. Milstein, 256 Nature (1975) 495; Davis, B., R. Dulbecco, H. Eisen, H. Ginsberg and W. Wood, Principles of Microbiology and Immunology, 2d ed., Harper & Row, New York, 1973.

Either the SCC-like material or antibody produced therefrom could be immobilized on a solid support. Numerous supports could be used, for example agarose resins (Sepharose, etc.), glass beads, etc. An immobilized antibody to SCC could act as a rapid and efficient purification tool to obtain pure SCC from crude sources. Likewise, pure antibody could be obtained utilizing immobilized SCC-like material. These immunoaffinity chromatographic methods are well established in the literature. The preceding illustrates examples of how immobilized ligands can be utilized but should not be construed to limit their usefulness. For example, immobilized SCC antibody could be used as a stripping agent to obtain SCC free serum.

The following examples describe various aspects of the collection, identification, purification and utilization of the SCC-like material. However, these examples are not intended to limit the usefulness of the newly invented material or techniques for isolation or utilization thereof.

EXAMPLE 1

Urine Collection

Urine samples were collected from the following groups of subjects: 5 human pregnant, 6 human female nonpregnant, and 7 human male. The nonpregnant group was further subdivided into 2 female smokers, 3 female smokers, 4 male nonsmokers, 3 male smokers, and 3 nonpregnant females who reported hormonal imbalances. Samples between 100 and 1000 ml were collected.

The urine specimens were filtered by the gravity filtration method. The supernatant was retained and the residue was discarded.

EXAMPLE 2

Radioimmunoassay of Urine Samples

The supernatants obtained above were assayed for the presence of the squamous cell carcinoma antigen using a radioimmunoassay purchased from Abbott Laboratories, Diagnostics Div., North Chicago, IL (Product SCC-RIA, Catalog #1376-22). This is a competitive assay, where a constant amount of $I^{125}$ labelled squamous cell carcinoma antigen competes with nonlabelled antigen on an anti squamous cell carcinoma antigen antibody. Free antigen is separated from antigen bound to antibody by a second antibody which will precipitate only the primary antigen-antibody complex. The manufacturer's instructions were followed exactly as provided.

The kit contains $I^{125}$ labelled SCC, SCC antiserum (Rabbit), Second antibody (Goat), SCC standard (Human) 0 ng/ml, SCC standards (Human): 1.5, 5, 15, 50 and 150 ng/ml, and instructions for use.

One hundred microliters of standards or specimens were pipetted into the assigned tubes. Two hundred microliters of SCC $I^{125}$ reagent were then pipetted into all tubes. One hundred microliters of SCC antiserum (Rabbit) were pipetted into each tube. The tubes were vortexed, covered, and incubated for 20 to 30 hours at room temperature. After 20 to 30 hours, 0.5 ml of second antibody (Goat) was added to each tube. The tubes were vortexed and then allowed to incubate for 10 to 30 minutes at room temperature. The tubes were centrifuged at 1000 to $2500 \times g$ for 20 minutes. After centrifugation, the tubes were immediately decanted and the pellet retained. The tubes were then read in a suitable well-type gamma scintillation counter.

EXAMPLE 3

Identification of SCC in Urine

A tabular identification of SCC assay results for the samples stated in Example 1 are presented in Table 1. The results shown in Table 1 suggest several conclusions. First, SCC appears to be present in high levels in human female urine. The normal limit for human serum is set at 2.5 ng/ml i.e., values above 2.5 ng/ml have been associated with a cancerous state. Females who smoke have urine SCC levels approximately twice the levels of their nonsmoking counterparts. Pregnancy does not appear to substantially increase the urine SCC levels. However, this does not preclude the possibility that urine SCC levels vary through the pregnancy period. This situation would not be an uncommon observation. An example to illustrate this point is human chorionic gonadotropin whose levels rise and fal dramatically through pregnancy. Hormonal imbalances in nonpregnant females appears to substantially increase the levels of SCC in the urine. Normal male urine does not appear to have elevated levels of SCC. However, this possibility is not precluded because of the small sample population. Smoking in normal males does not appear to increase the SCC level in urine. The results and conclusions from the experiments stated in Example 3 do not preclude various additional possibilities. Among these possibilities but not totally inclusive are: SCC levels in human female urine may be menstrual cycle dependent, urine levels may indicate the existence of cancerous or precancerous states (allowing for noninvasive testing procedure), and urine levels may indicate the presence of hormonal imbalances.

TABLE 1

SCC IN HUMAN URINE SPECIMENS

| Subject (ng/ml) | Sex | Smoker | Pregnant | SCC Level |
| --- | --- | --- | --- | --- |
| J. W. | F | N | Y | 120 |
| M. N. | F | N | Y | 60 |
| H. B. | F | N | Y | 60 |
| A. W. | F | N | Y | 46 |
| C. P. | F | N | Y | 240 |
| L. C. | F | N | N | 90 |
| M. E. | F | N | N | 80 |
| A. S. | F | Y | N | 200 |
| J. H.* | F | Y | N | 380 |
| P. P.* | F | Y | N | 440 |
| E. B.* | F | N | N | 460 |
| T. F. | M | N | N | 3 |
| J. B. | M | N | N | 3 |
| E. E. | M | N | N | 3 |
| T. D. | M | N | N | 2 |
| D. M. | M | Y | N | 3 |
| S. H. | M | Y | N | 3 |
| T. B. | M | Y | N | 3 |

*hormonal imbalances reported by subject

EXAMPLE 4

Comparison of Authentic SCC with Urine SCC by Gel Filtration

Gel filtration is a common method for obtaining the molecular weight of a protein. This method is based upon small proteins fitting into the pores of the gel filtration matrix and thus causing retardation in flow rate while larger proteins pass through unobstructed.

A 2.5×22.5 cm column of Sephadex G-150 (Sigma Chemical Co.) was equilibrated with 0.05 M potassium phosphate pH 7.0. Porcine pancreas amylase (molecular weight 45,000 daltons) was used to calibrate the column due to its molecular weight similarity with the SCC antigen. The molecular weight of SCC isolated from squamous cell carcinoma tissue has been reported to be 48,000 daltons (Kato & Torigoe, 1977). The column was run at room temperature and fraction sizes were 120 drops. Experiments were conducted in at least duplicate. The peak of porcine pancreas amylase activity was always found in tube #16. The peaks of SCC activity from human female urine as well as an authentic SCC sample from Abbott were always found in tube #14. These results suggested that the SCC from human female urine has a very similar or identical molecular weight as authentic SCC. Molecular weight comparison is often used to determine the identity between proteins. For example, Hussa et al, 1986, used molecular weights to suggest the identity between SCC obtained from cervical carcinoma tissue and the CaSki cervical carcinoma cell line. Hence, the experiments outlined above in Example 4 suggest that the SCC from human female urine is the same protein as that isolated from squamous cell carcinoma tissue.

EXAMPLE 5

Comparison of Authentic SCC with Urine SCC by Ion Exchange

Another property of proteins which is used to suggest identity or uniqueness is their isoelectric point. An exact value can only be obtained when sufficient quantities are available for isoelectric focusing techniques. However, close estimates can be obtained by ion exchange chromatography. Proteins tend to bind to anion exchangers at pHs above their isoelectric point and tend not to bind at pHs below their isoelectric point.

Ten fold concentrated (see Example 6) human female urine was gently stirred with Whatman QA-52 anion exchanger at pH was gently stirred with Whatman QA-52 anion exchanger at pH 6.5 (1 g of exchanger/1 ml conc. urine) at room temperature. The anion exchanger was separated from the urine by gravity filtration and the supernatent was assayed for SCC as described in Example 2. Assay results indicated the supernatant to be void of SCC activity. Ten fold concentrated human female urine was then gently stirred with Whatman QA-52 anion exchanger at pH 5.9 (1 g of exchanger/1 ml conc. urine) at room temperature. The anion exchanger was separated from the urine by gravity filtration and the supernatant was assayed for SCC as described in Example 2. Assay results indicated quantitative recovery of SCC in the supernatent. The above experimental results suggest the isoelectric point of human female urine SCC to be between 5.9 to 6.5. This is in excellent agreement with the published values of 5.9-6.2 and 6.3-6.6 for SCC from squamous cell carcinoma tissue (Kato et al, 1984). Hence, the experiments outlined above further suggest that the SCC from human female urine is the same protein as that isolated from squamous cell carcinoma tissue.

EXAMPLE 6

Crude Squamous Cell Carcinoma Antigen (SCC)

The following is an example of a procedure to manufacture crude SCC from human female urine: Human female urine is collected and immediately frozen for storage. When ready to use, the urine was allowed to thaw to yield the desired quantity in weight. Every container was inspected for satisfactory physical characteristics. All equipment was inspected for cleanliness and if needed, equipment for final filtration was steam cleaned. SCC radioimmunoassays were run as described in Example 2. Only samples which showed greater than 80 ng/ml were accepted. The urine was then pooled and filtered using a filter of at least 0.8 micron retention. 0.5-1.0% (w/v) Celite was used as a filtering aid. The filtrate was then concentrated to approximately 2,000.00 ng/ml using a concentration device. (Amicon Stirred Cell Model 8400, utilizing a YMIO membrane) with a molecular weight cut off less than 10,000 daltons. The concentrate was then dialyzed against $10 \times 10^{-3}$M potassium phosphate buffer pH 6.9 (100 fold) overnight (5° C.). The dialysate was then filtered into a steam cleaned tank through a 0.45 micron filter and filled into clean bottles at desired levels. Product was either stored frozen at −20° C. or lyophilized according to Example 7.

EXAMPLE 7

Lyophilization Procedures

Industrial vacuum dryers (Hull Corporation, Hatboro, PA, model 651VC36F40) were utilized for the lyophilization process. The shelf temperature was lowered to a minimum of −29° C. prior to loading samples. The product was then loaded and once all product temperatures had reached −29° C. or below, the shelf temperature was set to +5° C. The temperature was maintained at +5° C. until all product reached −1° C. The temperature was then increased to +16° C. where it was maintained until all product reached +10° C. At this point, the temperature was increased to +27° C.

and maintained until all product temperatures reached +21° C. The shelf temperature was then increased to +43° C. and maintained until all product temperatures reached +38° C. When the product temperature reached +38° C. on all product readings, then an additional 12 hours was required. After the dryer cycle was completed the dryers were vented and product was unloaded.

EXAMPLE 8

Standard Grade Squamous Cell Carcinoma Antigen (SCC)

The following is an example of a procedure to manufacture partially purified SCC from human female urine: The procedure for crude SCC as described in Example 6 was followed through the concentration step. The concentrate was then applied to a Sephadex G-150 sizing column, which has been pre-calibrated using porcine pancreatic amylase (Prod. No. A6255, Sigma Chemical Co.) which has a molecular weight close to that of SCC (approximately 70 ml Sephadex per ml of concentrated urine). Based upon this precalibration, tubes were collected and assayed for SCC activity using the radioimmunoassay described in Example 2. The SCC positive peak was pooled. The pool was concentrated to approximately 2,000 ng/ml using a molecular weight cut off less than 10,000 and filtered through a 0.45 micron filter. The product was then filled into bottles at 1 microgram/bottle and stored frozen or lyophilized as described in Example 7.

EXAMPLE 9

Tumor Marker Control

The following is an example of a procedure to manufacture a tumor marker control containing SCC in a human serum base: Sufficient containers of human serum to yield desired weight were allowed to thaw. Total protein was between 5.0 and 6.0 g/dl. The human serum did not show any visible signs of bacterial contamination. Serum and unpurified stock solutions were then tested for endogenous levels of all constituents stated below. The pH of the serum was adjusted to 6.1 (using 4N hydrochloric acid) and stirred until the pH reached approximately 6.8. The solution was made $1.5 \times 10^{-2}$ M in Hepes buffer and the pH adjusted to 6.8-7.0. 0.1 to 0.5% of Celite was added to the pooled serum, mixed, and filtered through pads of at least 0.5 microns. The following constituents were then added to the desired levels while mixing the pool at a medium speed: alphafeto protein, carcinoembryonic antigen, CA 125, CA 19-9, CA 50, CA 15-3, ferritin, beta-hCG, immunoreactive elastase, prostatic acid phosphatase, tissue polypeptide antigen, and human female urine (as a source for SCC). The pool was filtered through a 0.45 micron filter and filled at 5.2 ml per vial. The product was then lyophilized as described in Example 7.

Accelerated stability studies were conducted on at least three distinct lots of the tumor marker controls. Samples were incubated at 37° C. and values extrapolated to 5° C. Five weeks at 37° C. was considered to be equivalent to four years at 5° C. The results of these experiments showed the SCC constituent in the product to be stable for a minimum of 4 years at 5° C.

What is claimed is:

1. A method of isolation of squamous cell carcinoma-like antigen from normal human female urine comprising:
    a) selection of normal human female urine samples with concentrations of squamous cell carcinoma-like antigen of greater than approximately 40 ng/ml; and
    b) either concentration of the urine or separation of the antigen from the urine.

2. The method of claim 1 wherein the selection comprises the use of immunoassay procedures.

3. The method of claim 1 wherein the separation comprises the use of column chromatography techniques.

4. The method of claim 1 wherein the human samples selected contain a minimum of approximately 80 ng/ml.

5. The method of claim 1 wherein the purpose for using the antigen is manufacture of a control material, manufacture of a standard or use as an immunogen.

* * * * *